(12) United States Patent
Nakanishi et al.

(10) Patent No.: US 9,417,183 B2
(45) Date of Patent: Aug. 16, 2016

(54) TERAHERTZ WAVE TEMPORAL WAVEFORM ACQUISTION APPARATUS

(71) Applicant: HAMAMATSU PHOTONICS K.K., Hamamatsu-shi, Shizuoka (JP)

(72) Inventors: Atsushi Nakanishi, Hamamatsu (JP); Kazuki Horita, Hamamatsu (JP); Takashi Yasuda, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/982,022

(22) Filed: Dec. 29, 2015

(65) Prior Publication Data

US 2016/0202179 A1    Jul. 14, 2016

(30) Foreign Application Priority Data

Jan. 8, 2015 (JP) ................. 2015-002053

(51) Int. Cl.
| | |
|---|---|
| G01J 5/02 | (2006.01) |
| G01N 21/3586 | (2014.01) |
| G01N 21/47 | (2006.01) |
| G01N 21/3563 | (2014.01) |
| G01N 21/3581 | (2014.01) |

(52) U.S. Cl.
CPC ........ *G01N 21/3586* (2013.01); *G01N 21/3563* (2013.01); *G01N 21/3581* (2013.01); *G01N 21/4795* (2013.01); *G01N 2201/06113* (2013.01)

(58) Field of Classification Search
CPC .......... G01N 21/3581; G01N 21/4795; G01N 21/3563

USPC .......................................... 250/352
See application file for complete search history.

(56) References Cited

U.S. PATENT DOCUMENTS

| | | | |
|---|---|---|---|
| 8,737,439 B2 * | 5/2014 | Wilk | H01S 3/10 372/18 |
| 2009/0225312 A1 * | 9/2009 | Formanek | G01J 3/02 356/326 |

FOREIGN PATENT DOCUMENTS

| | | |
|---|---|---|
| EP | 2 098 839 | 9/2009 |
| WO | WO 2008/075696 | 6/2008 |

OTHER PUBLICATIONS

P.Y. Han et al., "Free-space coherent broadband terahertz time-domain spectroscopy", Meas. Sci. Technol. 12, 2001, p. 1747-p. 1756.

* cited by examiner

*Primary Examiner* — David Porta
*Assistant Examiner* — Meenakshi Sahu
(74) *Attorney, Agent, or Firm* — Drinker Biddle & Reath LLP

(57) ABSTRACT

A terahertz wave temporal waveform acquisition apparatus includes a light source, a branch part, a terahertz wave generation element, a terahertz wave detection element, a delay providing medium, a temperature adjustment unit, and an analysis unit. The delay providing medium is disposed on an optical path of a terahertz wave from the terahertz wave generation element to the terahertz wave detection element, is formed of a material of which a refractive index for the terahertz wave depends on the temperature, and provides a delay according to the temperature to the terahertz wave.

8 Claims, 11 Drawing Sheets

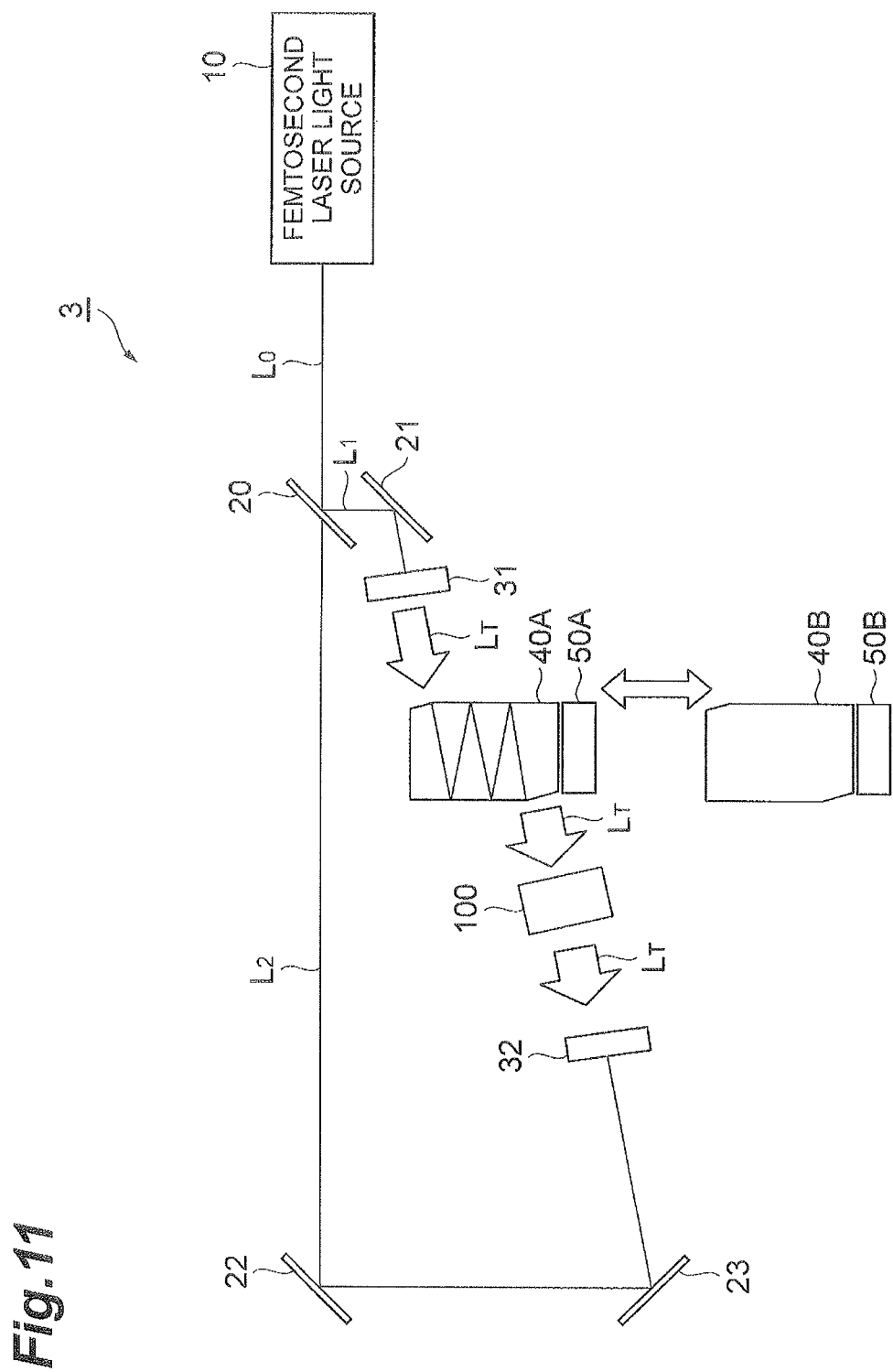

TERAHERTZ WAVE TEMPORAL WAVEFORM ACQUISTION APPARATUS

BACKGROUND OF THE INVENTION

1. Field of the Invention

The present invention relates to a terahertz wave temporal waveform acquisition apparatus.

2. Related Background Art

A terahertz wave is an electromagnetic wave having a frequency of about 0.01 THz to 100 THz corresponding to a region in the middle of a light wave and a radio wave, and has an intermediate nature between the light wave and the radio wave. As an application of the terahertz wave, research has been conducted on a technique for obtaining information on a measurement object by measuring a temporal waveform of an electric field amplitude of the terahertz wave passed through or reflected by the measurement object.

A general technique for measuring the information on the measurement object by using the terahertz wave is as follows. That is, pulsed light output from a light source (such as femtosecond laser light source) is branched by a branch part into two beams, i.e., pump light and probe light. The pump light is input to a terahertz wave generation element (for example, nonlinear optical crystal or photoconductive antenna element), and according to this, the terahertz wave generation element generates the pulsed terahertz wave. The generated terahertz wave obtains the information on the measurement object (for example, absorption coefficient, refractive index) by passing through or being reflected by the measurement object, and after that, the terahertz wave is input to a terahertz wave detection element (for example, electrooptical crystal or photoconductive antenna element) at the substantially same timing as the probe light. The terahertz wave detection element to which the terahertz wave and the probe light have been input detects a correlation value between the terahertz wave and the probe light.

When the electrooptical crystal is used as the terahertz wave detection element, the terahertz wave and the probe light are coupled by a coupling part and input to the electrooptical crystal, a birefringence is induced in the electrooptical crystal along with propagation of the terahertz wave, and the birefringence changes a polarization state of the probe light. The change of the polarization state of the probe light in the electrooptical crystal is detected, and thus the electric field amplitude of the terahertz wave is detected and the information on the measurement object is obtained.

Further, when the photoconductive antenna element is used as the terahertz wave detection element, a current expressing the correlation value between the terahertz wave and the probe light is generated between two electrodes of the photoconductive antenna element according to the inputs of the terahertz wave and the probe light. A spectrum of the terahertz wave is obtained, based on the correlation value, and in addition, the information on the measurement object is obtained.

Generally, the pulse width of the terahertz wave is about a picosecond, whereas, the pulse width of the probe light is about a femtosecond, and the pulse width of the probe light is narrower than that of the terahertz wave by several digits. According to this, the input timing of the terahertz wave or the probe light to the terahertz wave detection element is swept so that the temporal waveform of the electric field amplitude of the terahertz wave is obtained.

Non-Patent Document 1: P. Y. Han and X.-C. Zhang, "Free-space coherent broadband terahertz time-domain spectroscopy", Meas. Sci. Technol. 12, pp. 1747-1756 (2001)

SUMMARY OF THE INVENTION

When the input timing of the terahertz wave or the probe light to the terahertz wave detection element is swept, a mechanical delay providing mechanism which has been provided in the middle of the optical path of the pump light or the probe light is used. In the mechanical delay providing mechanism, a turning back mirror arranged on a stage can be moved along a predetermined axis, the optical path length is extended or shortened by mechanically moving the turning back mirror, and a delay according to the optical path length is provided to the light. Since it is difficult to miniaturize the stage, it is difficult to miniaturize the terahertz wave temporal waveform acquisition apparatus including such a mechanical delay providing mechanism.

The present invention has been made to solve the above problem, and an object thereof is to provide a terahertz wave temporal waveform acquisition apparatus which can be easily miniaturized.

A terahertz wave temporal waveform acquisition apparatus according to the present invention includes (1) a light source outputting pulsed light, (2) a branch part branching the pulsed light output from the light source, outputting one beam of the branched light as pump light, and outputting another beam of the branched light as probe light, (3) a terahertz wave generation element generating and outputting a terahertz wave by inputting the pump light output from the branch part, (4) a terahertz wave detection element inputting the terahertz wave output from the terahertz wave generation element and passed through or reflected by a measurement object, inputting the probe light output from the branch part, and detecting a correlation value between the terahertz wave and the probe light, (5) a delay providing medium disposed on an optical path of the terahertz wave from the terahertz wave generation element to the terahertz wave detection element, formed of a material of which a refractive index for the terahertz wave depends on the temperature, and configured to provide a delay according to the temperature to the terahertz wave, (6) a temperature adjustment unit configured to adjust the temperature of the delay providing medium, and (7) an analysis unit obtaining a temporal waveform of an electric field amplitude of the terahertz wave input to the terahertz wave detection element based on the correlation value detected by the terahertz wave detection element when the temperature of the delay providing medium is set to each value by the temperature adjustment unit.

According to the present invention, a terahertz wave temporal waveform acquisition apparatus which can be easily miniaturized is provided.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 11 is a diagram of a configuration of a terahertz wave temporal waveform acquisition apparatus 3 according to a third embodiment.

DESCRIPTION OF THE EMBODIMENTS

Embodiments of the present invention will be described in detail below with reference to the attached drawings. In the description of the drawings, the same components are denoted with the same reference symbols, and overlapping description will be omitted.

First Embodiment

Figure 1:
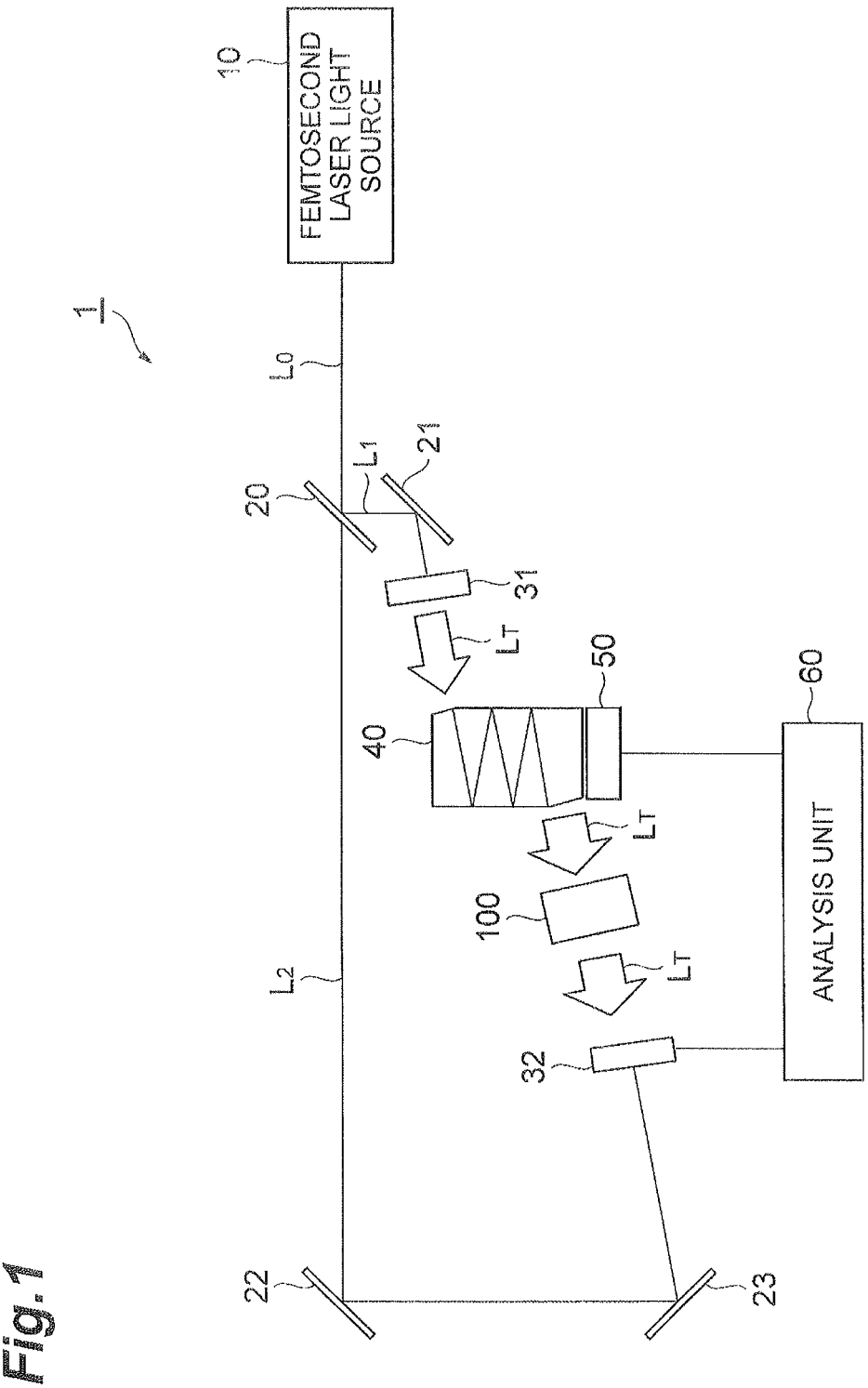
FIG. 1 is a diagram of a configuration of a terahertz wave temporal waveform acquisition apparatus 1 according to a first embodiment.

FIG. 1 is a diagram of a configuration of a terahertz wave temporal waveform acquisition apparatus 1 according to a first embodiment. The terahertz wave temporal waveform acquisition apparatus 1 according to the first embodiment includes a light source 10, a branch part 20, mirrors 21 to 23, a terahertz wave generation element 31, a terahertz wave detection element 32, a delay providing medium 40, a temperature adjustment unit 50, and an analysis unit 60, and is configured to obtain information on a measurement object 100.

The light source 10 outputs pulsed light $L_0$ with a constant repetition period T, and preferably, the light source 10 is a femtosecond pulse laser light source for outputting pulsed laser light having a pulse width of about a femtosecond. The branch part 20 branches the pulsed light $L_0$ output from the light source 10, outputs one beam of the branched light to the mirror 21 as pump light $L_1$, and outputs another beam of the branched light to the mirror 22 as probe light $L_2$. The branch part 20 is, for example, a beam splitter.

The terahertz wave generation element 31 inputs the pump light $L_1$ output from the branch part 20 and reflected by the mirror 21, and generates and outputs a terahertz wave $L_T$. The terahertz wave generation element 31 includes, for example, any one of a nonlinear optical crystal (such as ZnTe), a photoconductive antenna element (such as an optical switch using GaAs), a semiconductor (such as InAs), and a superconductor.

The terahertz wave $L_T$ output from the terahertz wave generation element 31 is an electromagnetic wave having a frequency of about 0.01 THz to 100 THz corresponding to a region between a light wave and a radio wave, and has an intermediate nature between the light wave and the radio wave. Further, the terahertz wave $L_T$ is generated with a constant repetition period T, and has a pulse width of about several picoseconds. The terahertz wave $L_T$ passes through the delay providing medium 40 and the measurement object 100, and is input to the terahertz wave detection element 32. By passing through the measurement object 100, the terahertz wave $L_T$ obtains information on the measurement object 100 (for example, absorption coefficient, refractive index).

The terahertz wave detection element 32 inputs the terahertz wave $L_T$ output from the terahertz wave generation element 31 and passed through the measurement object 100, and further, inputs the probe light $L_2$ output from the branch part 20 and reflected by the mirrors 22 and 23. The terahertz wave detection element 32 detects a correlation value between the input terahertz wave $L_T$ and the probe light $L_2$.

The delay providing medium 40 is disposed on an optical path of the terahertz wave $L_T$ from the terahertz wave generation element 31 to the terahertz wave detection element 32. The delay providing medium 40 may be disposed on an optical path between the terahertz wave generation element 31 and the measurement object 100, and on an optical path between the measurement object 100 and the terahertz wave detection element 32.

The delay providing medium 40 is formed from a material having a refractive index for the terahertz wave $L_T$ depending on the temperature. The delay providing medium 40 can provide a delay according to the temperature to the terahertz wave $L_T$. That is, the delay providing medium 40 can sweep terahertz wave input timing relative to probe light input timing to the terahertz wave detection element 32 by changing the temperature.

It is preferable that the delay providing medium 40 is formed from a material having high transmittance for the terahertz wave, small thermal expansion, and a large refractive index temperature change. As the material of the delay providing medium 40, in addition to silicon, glass, calcium fluoride, zinc selenide, barium fluoride, lithium fluoride, magnesium fluoride, calcite, germanium, magnesium oxide, diamond, crystal, sapphire, cycloolefin polymer, polyethylene, and Teflon (registered trademark) are exemplified.

The temperature adjustment unit 50 adjusts the temperature of the delay providing medium 40. For example, the temperature adjustment unit 50 includes a Peltier element, and can precisely set the temperature of the delay providing medium 40 to each value.

The analysis unit 60 inputs a correlation value detected by the terahertz wave detection element 32 when the temperature of the delay providing medium 40 is set to each value by the temperature adjustment unit 50. The analysis unit 60 obtains the temporal waveform of the electric field amplitude of the terahertz wave $L_T$ input to the terahertz wave detection element 32 based on the Correlation value at each temperature setting value.

The terahertz wave temporal waveform acquisition apparatus 1 operates as follows. The pulsed light $L_0$ output from the light source 10 with the constant repetition period T is branched by the branch part 20 into two light beams, i.e., the pump light $L_1$ and the probe light $L_2$. When the pump light $L_1$ output from the branch part 20 is reflected by the mirror 21 and input to the terahertz wave generation element 31, the terahertz wave $L_T$ is generated in the terahertz wave generation element 31.

The terahertz wave $L_T$ output from the terahertz wave generation element 31 passes through the delay providing medium 40 and the measurement object 100 and is input to the terahertz wave detection element 32. The probe light $L_2$ output from the branch part 20 is reflected by the mirrors 22 and 23 and input to the terahertz wave detection element 32.

The terahertz wave detection element 32 detects the correlation value between the input terahertz wave $L_T$ and the probe light $L_2$.

The temperature adjustment unit. 50 sets the temperature of the delay providing medium 40 disposed on the optical path of the terahertz wave $L_T$ to each value, and the terahertz wave detection element 32 detects the correlation value for each temperature setting value, and the detected correlation value is input to the analysis unit 60. Then, the analysis unit 60 obtains the temporal waveform of the electric field amplitude of the terahertz wave $L_T$ input to the terahertz wave detection element 32 based on the correlation values for respective temperature setting values. In addition, the information on the measurement object 100 is obtained based on the temporal waveform.

When the temporal waveform of the electric field amplitude of the terahertz wave $L_T$ is measured, an S/N ratio is generally improved by obtaining the temporal waveforms at a plurality of times and integrating the plurality of temporal waveforms. In the configuration of the present embodiment, the temporal waveforms of the electric field amplitude of the terahertz wave $L_T$ may be repeatedly obtained as the temperature of the delay providing medium 40 is changed from a low temperature to a high temperature, or conversely, the temporal waveforms of the electric field amplitude of the terahertz wave $L_T$ may be repeatedly obtained as the temperature of the delay providing medium 40 is changed from a high temperature to a low temperature. However, when the temporal waveform is obtained in a period in which the temperature is changed in one direction as the above cases, it takes time to change the temperature in the reverse direction and to return the temperature to the start temperature.

Therefore, in the present embodiment, it is preferable to obtain an integrated value of the temporal waveforms by alternately performing acquisition of the temporal waveform of the electric field amplitude of the terahertz wave $L_T$ by changing the temperature of the delay providing medium 40 from the low temperature to the high temperature, and acquisition of the temporal waveform of the electric field amplitude of the terahertz wave $L_T$ by changing the temperature of the delay providing medium 40 from the high temperature to the low temperature, and in this way, the temporal waveform with an excellent S/N can be obtained in a short time.

FIG. 2 to FIG. 7 are diagrams of configuration examples of the delay providing medium 40. The delay providing medium 40 shown in these figures inputs the terahertz wave $L_T$ from an input surface, allows the terahertz wave $L_T$ to be reflected and propagated internally, and after that, outputs the terahertz wave $L_T$ from an output surface to the outside. The number of reflections of the terahertz wave $L_T$ inside the delay providing medium 40 may be one, however, the plurality of numbers of reflections is preferable, because a delay variation amount due to the temperature change can be larger. Further, it is preferable from the viewpoint of loss reduction that the reflection of the terahertz wave $L_T$ in the delay providing medium 40 be total reflection.

Figure 2:
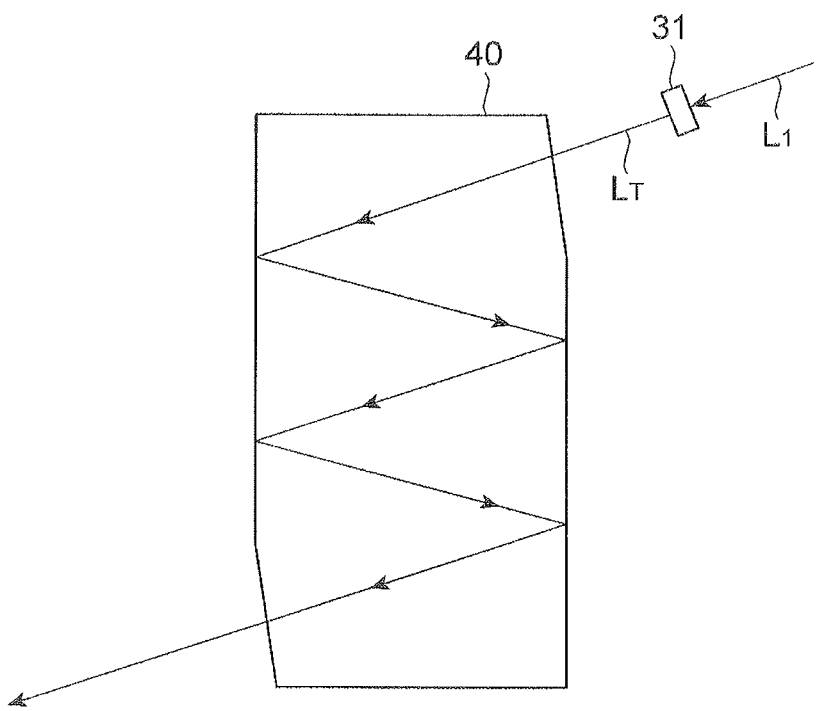
FIG. 2 is a diagram of a first configuration example of a delay providing medium 40.

In a first configuration example illustrated in FIG. 2, the terahertz wave $L_T$ is input from the input surface to the delay providing medium 40, and the medium reflects the terahertz wave $L_T$ four times by alternately using opposed two surfaces, and after that, the terahertz wave $L_T$ is output from the output surface to the outside.

Figure 3:
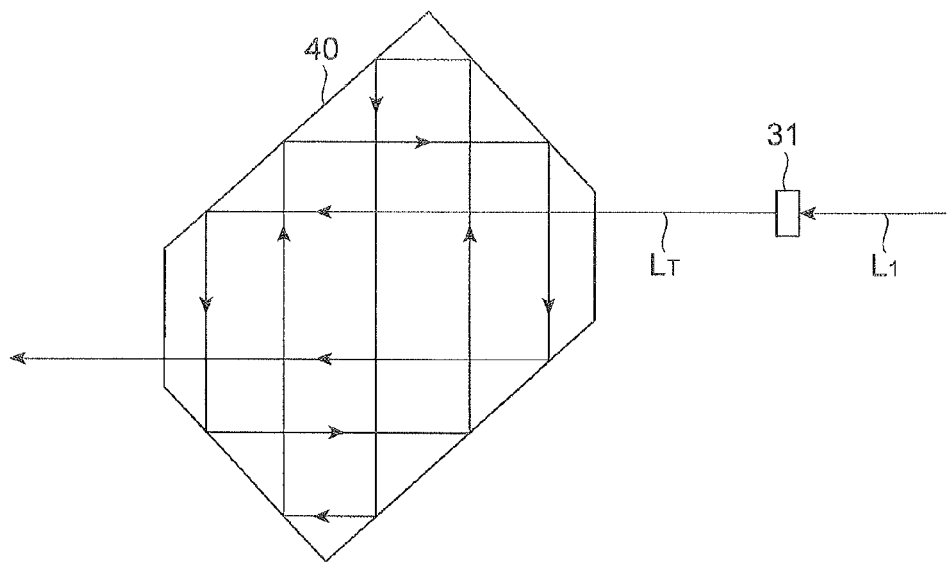
FIG. 3 is a diagram of a second configuration example of the delay providing medium 40.

In a second configuration example illustrated in FIG. 3, the terahertz wave $L_T$ is input from the input surface to the delay providing medium 40, and the medium reflects and propagates around the terahertz wave $L_T$ ten times by sequentially using four surfaces, and after that, the terahertz wave $L_T$ is output from the output surface to the outside. The delay variation amount in the second configuration example can be larger than that in the first configuration example even when the delay providing medium 40 of which the size is nearly the same is used.

Figure 4:
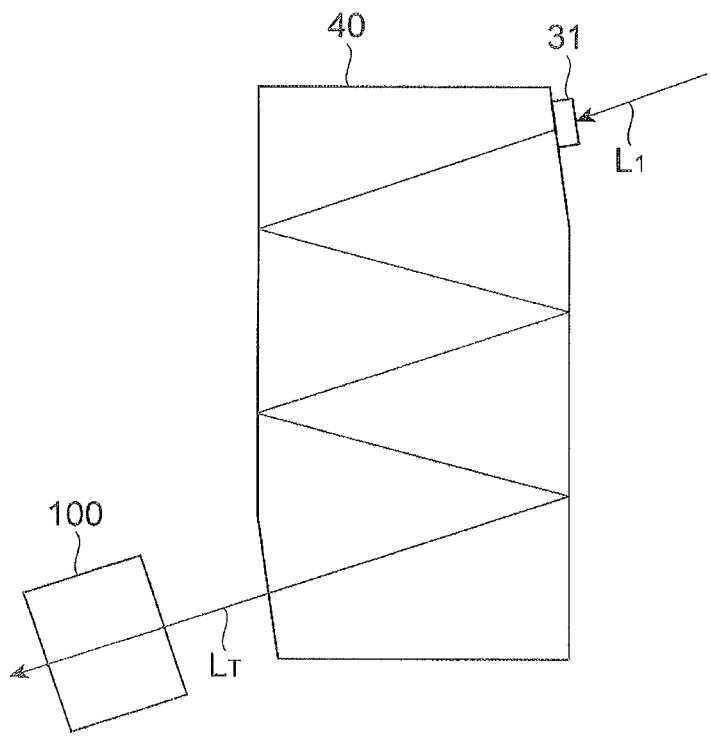
FIG. 4 is a diagram of a third configuration example of the delay providing medium 40.

In a third configuration example illustrated in FIG. 4, the terahertz wave generation element 31 is integrally provided on the input surface of the delay providing medium 40. In this configuration example, incident loss of the terahertz wave $L_T$ at the input surface of the delay providing medium 40 can be reduced, and therefore, the temporal waveform of the electric field amplitude of the terahertz wave $L_T$ can be efficiently obtained.

Figure 5:
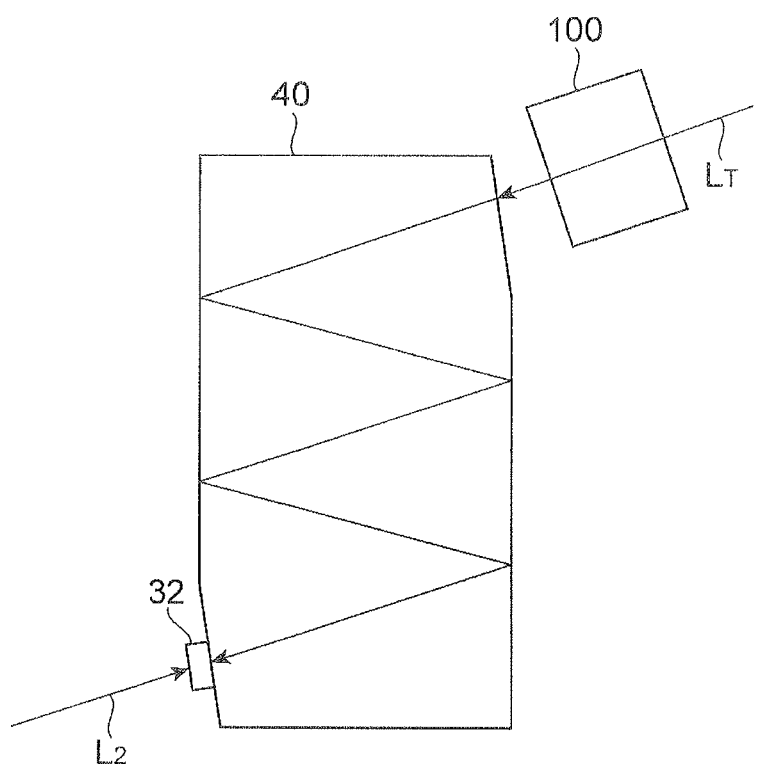
FIG. 5 is a diagram of a fourth configuration example of the delay providing medium 40.

In a fourth configuration example illustrated in FIG. 5, the terahertz wave detection element 32 is integrally provided on the output surface of the delay providing medium 40. In this configuration example, emission loss of the terahertz wave $L_T$ at the output surface of the delay providing medium 40 can be reduced, and therefore, the temporal waveform of the electric field amplitude of the terahertz wave $L_T$ can be efficiently obtained.

Figure 6:
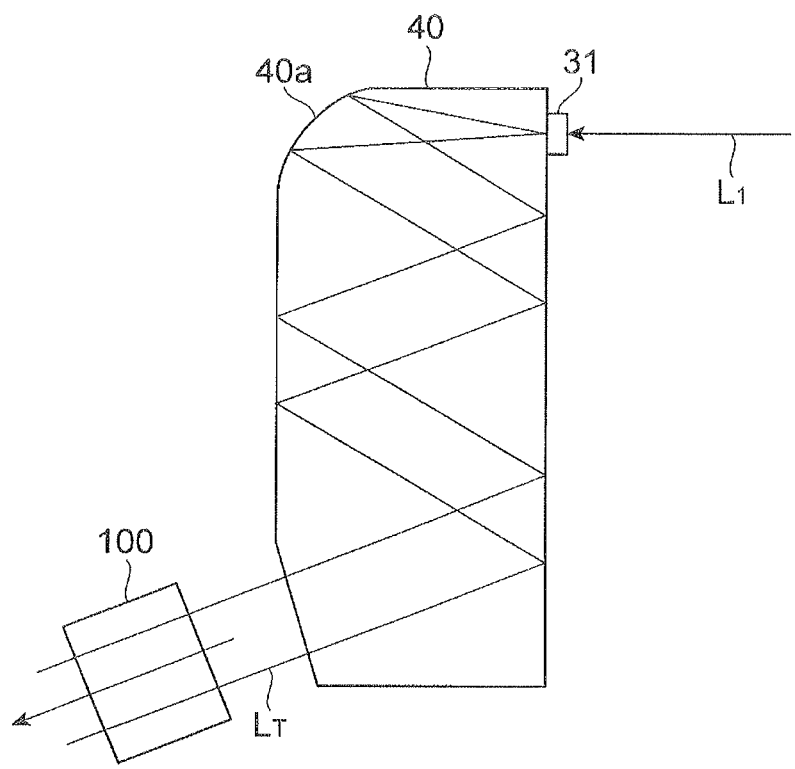
FIG. 6 is a diagram of a fifth configuration example of the delay providing medium 40.

In a fifth configuration example illustrated in FIG. 6, the delay providing medium 40 has a reflection surface 40a which changes the terahertz wave $L_T$ to parallel light when the medium reflects and propagates the terahertz wave $L_T$ therein—in this configuration example, as a case where the terahertz wave generation element 31 is a photoconductive antenna element, when terahertz wave $L_T$ output from the terahertz wave generation element 31 is divergent light, the terahertz wave $L_T$ can be the parallel light at the time of the reflection by the reflection surface 40a.

Figure 7:
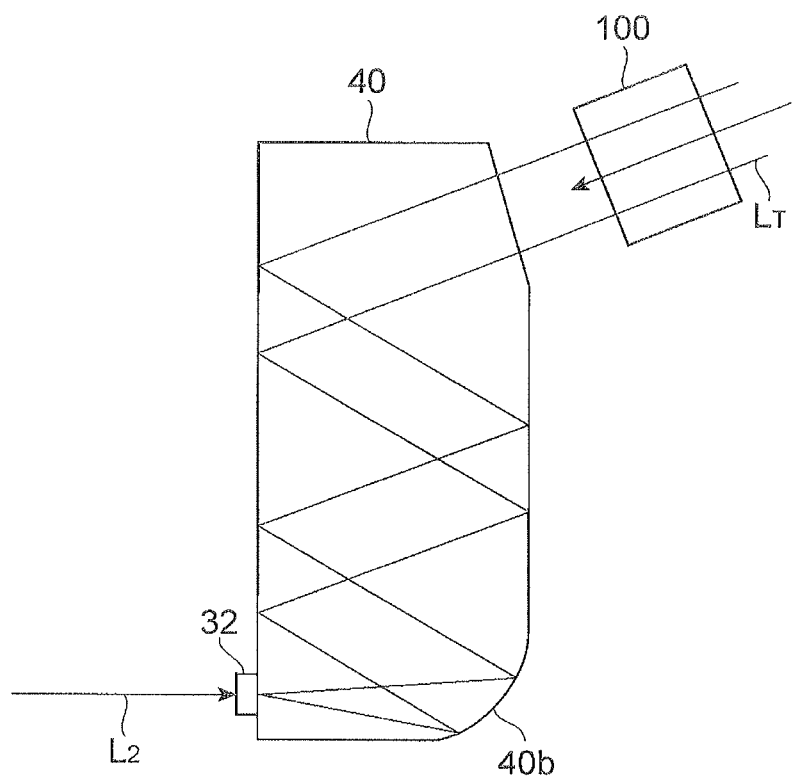
FIG. 7 is a diagram of a sixth configuration example of the delay providing medium 40.

In a sixth configuration example illustrated in FIG. 7, the delay providing medium 40 has a reflection surface 40b which changes the terahertz wave $L_T$ to convergent light when the medium reflects and propagates the terahertz wave $L_T$ therein. In this configuration example, as a case where the terahertz wave detection element 32 is a photoconductive antenna element, when it is preferable that the terahertz wave $L_T$ input to the terahertz wave detection element 32 be the convergent light, the terahertz wave $L_T$ can be the convergent light at the time of the reflection by the reflection surface 40b.

When both the terahertz wave generation element 31 and the terahertz wave detection element 32 are photoconductive antenna elements, it is preferable that the delay providing medium 40 have both the reflection surface 40a which converts the terahertz wave $L_T$ divergently output from the terahertz wave generation element 31 into the parallel light, and the reflection surface 40b which converts the terahertz wave $L_T$, which has been converted into the parallel light, into the convergent light.

As an example of the delay providing medium 40, a case is assumed where the material is silicon and a geometric distance along the optical path of the terahertz wave $L_T$ from the input surface to the output surface is 450 mm. When the temperature of such a delay providing medium 40 is changed from 20° C. to 40° C., the refractive index changes by about 0.0032, and the optical path length changes by 1.44 mm. Since a change amount of 1.44 mm of the optical path length corresponds to a time width of 4.8 ps, this is enough to obtain the temporal waveform of the electric field amplitude of the terahertz wave $L_T$.

The terahertz wave temporal waveform acquisition apparatus 1 according to the present embodiment can sweep the terahertz wave input timing to the terahertz wave detection element 32 by setting the temperature of the delay providing medium 40 to each value. The terahertz wave temporal waveform acquisition apparatus 1 according to the present embodiment can be more easily miniaturized than a conventional apparatus in which a mechanical delay providing mechanism is used.

Figure 8:
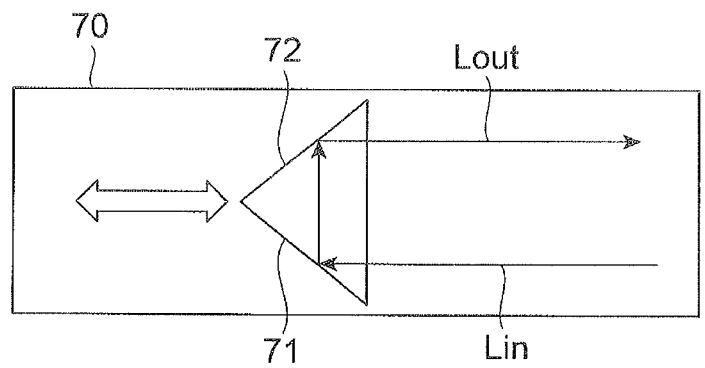
FIG. 8 is a diagram of a configuration of a mechanical delay providing mechanism 70.

Further, as illustrated in FIG. 8, the mechanical delay providing mechanism 70 in the conventional apparatus reflects input light $L_{in}$ by mirrors 71 and 72 and changes it to output light $L_{out}$, and changes the optical path length by moving the mirrors 71 and 72 along the arrow direction in the figure. In the mechanical delay providing mechanism 70, the direction of the output light $L_{out}$ is fixed to be opposite to the direction of the input light $L_{in}$.

Figure 9A:
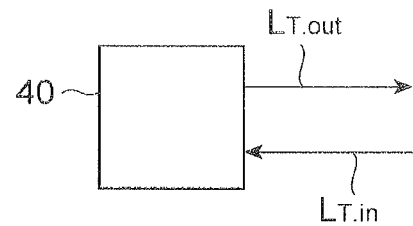
FIG. 9A to FIG. 9C are diagrams of examples of input/output directions of terahertz wave in the delay providing medium 40.
Figure 9B:
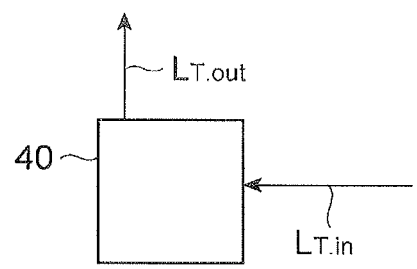
Figure 9C:
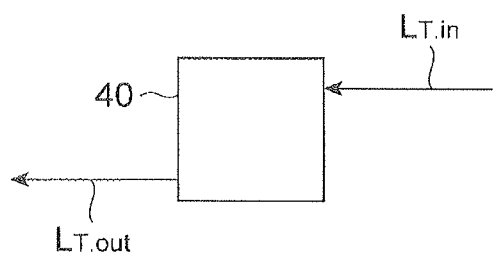

Whereas, as illustrated in FIG. 9A to FIG. 9C, the delay providing medium 40 in the terahertz wave temporal waveform acquisition apparatus 1 according to the present embodiment can variously set the direction of the output terahertz wave $L_{T\_out}$ relative to the direction of the input terahertz wave $L_{T\_in}$, and accordingly, degree of freedom for arrangement of an optical system is large. Also at this point, the terahertz wave temporal waveform acquisition apparatus 1 according to the present embodiment can be more miniaturized than a conventional apparatus using a mechanical delay providing mechanism.

Second Embodiment

Figure 10:
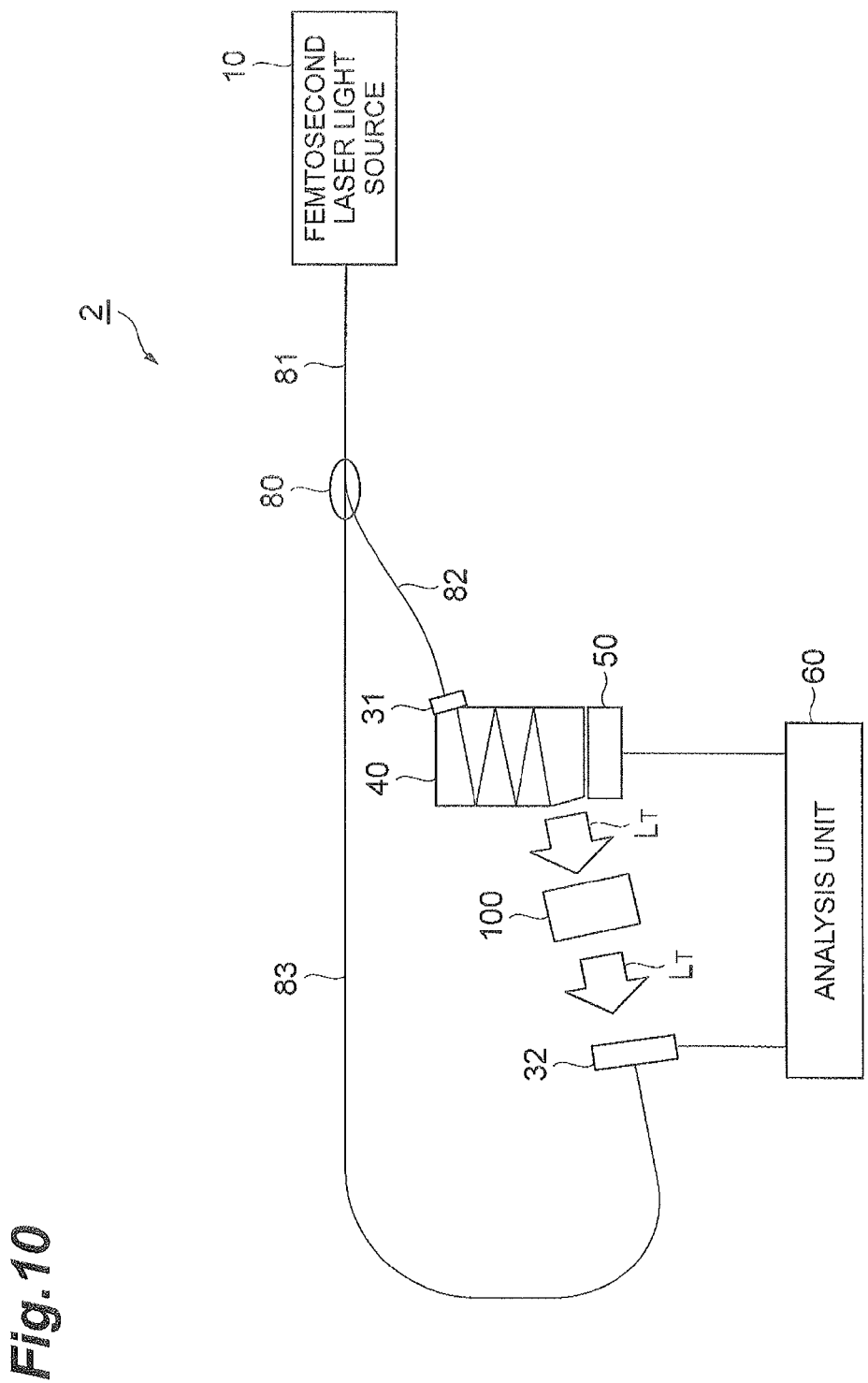
FIG. 10 is a diagram of a configuration of a terahertz wave temporal waveform acquisition apparatus 2 according to a second embodiment.

FIG. 10 is a diagram of a configuration of a terahertz wave temporal waveform acquisition apparatus 2 according to a second embodiment. The terahertz wave temporal waveform acquisition apparatus 2 according to the second embodiment includes a light source 10, a terahertz wave generation element 31, a terahertz wave detection element 32, a delay providing medium 40, a temperature adjustment unit 50, an analysis unit 60, an optical fiber coupler 80, and optical fibers 81 to 83, and obtains information on a measurement object 100.

The terahertz wave temporal waveform acquisition apparatus 2 according to the second embodiment has following points different from those of the configuration of the first embodiment illustrated in FIG. 1 including a point in which the optical fiber coupler 80 is provided as a branch part, a point where the pulsed light guiding optical fiber 81 guides the pulsed light from the light source 10 to the optical fiber coupler 80, a point where the pump light guiding optical fiber 82 guides the pump light from the optical fiber coupler 80 to the terahertz wave generation element 31, a point where the probe light guiding optical fiber 83 guides the probe light from the optical fiber coupler 80 to the terahertz wave detection element 32, and a point where the terahertz wave generation element 31 is integrally provided on an input surface of the delay providing medium 40.

The terahertz wave temporal waveform acquisition apparatus 2 according to the second embodiment provides an effect similar to that of the configuration of the first embodiment, and in addition, the following effect is provided by including the optical fibers 81 to 83. That is, in the second embodiment, the pulsed light output from the light source 10 and the pump light and the probe light output from the optical fiber coupler 80 are guided by the optical fibers and do not propagate in a free space, and therefore, a problem of axis deviation can be prevented. Thus, the temporal waveform is measured with high stability.

Here, in the present embodiment, when the temperature is transmitted from the delay providing medium 40 to the optical fiber 82, the refractive index of the pump light guiding optical fiber 82 is changed, delay time of the pump light guided by the pump light guiding optical fiber is changed, and as a result, there is a possibility that appropriate time delay is not given. Therefore, it is preferable to thermally separate the terahertz wave generation element 31 and the pump light guiding optical fiber 82 from each other.

Third Embodiment

FIG. 11 is a diagram of a configuration of a terahertz wave temporal waveform acquisition apparatus 3 according to a third embodiment. The terahertz wave temporal waveform acquisition apparatus 3 according to the third embodiment includes a plurality of delay providing media in the configuration of the first embodiment. In FIG. 11, two delay providing media 40A and 40B are illustrated, and further, a temperature adjustment unit 50A for adjusting a temperature of the delay providing medium 40A and a temperature adjustment unit 50B for adjusting a temperature of the delay providing medium 40B are illustrated.

In the present embodiment, the plurality of delay providing media is arranged on an optical path of the terahertz wave $L_T$ from the terahertz wave generation element 31 to the terahertz wave detection element 32 one by one, the temperature of the arranged delay providing medium is set to each value and a temporal waveform of an electric field amplitude of the terahertz wave is obtained, and an integrated value of the temporal waveform is obtained. When the two delay providing media 40A and 40B are used, they are alternately arranged on the optical path of the terahertz wave $L_T$.

The terahertz wave temporal waveform acquisition apparatus 3 according to the third embodiment provides an effect similar to that of the configuration of the first embodiment, and in addition, the following effect is provided by including the plurality of delay providing media. That is, when the temporal waveform is obtained only in a period when the temperature of the delay providing medium is changed in one direction in a case where a single delay providing medium is included, it takes time to change the temperature in the reverse direction and return it to the start temperature, on the other hand, in order to solve the problem, in the third embodiment, the two same delay providing media of which the temperatures are set to be the same are prepared and inserted to the optical path of the terahertz wave by alternately switching them, and accordingly, time for the integration measurement can be shortened.

Specifically, first, the first delay providing medium 40A is inserted in the optical path of the terahertz wave, the temperature of the delay providing medium 40A is swept from a low temperature to a high temperature (for example, from 20° C. to 40° C.), and the temporal waveform is measured. When the first sweep has been finished (for example, when the temperature of the delay providing medium 40A reaches 40° C.), the delay providing medium 40A is switched to the delay providing medium 40B which has been waited as having the temperature of 20° C. In this way, the second temporal waveform can be obtained from the time axis in the same direction in the completely same sweep start delay time. During the second sweep, the temperature of the delay providing medium 40A is lowered to 20° C. At the timing when the second weep is finished, the delay providing medium is switched to the delay providing medium 40A again, and similarly, the temporal waveform is obtained. By alternately repeating the above procedures, the time for the integration, measurement can be shortened.

The terahertz wave temporal waveform acquisition apparatus according to the present invention is not limited to the above-mentioned embodiments and configuration examples, and can be variously modified.

A terahertz wave temporal waveform acquisition apparatus according to the embodiments includes (1) a light source which outputs pulsed light, (2) a branch part which branches the pulsed light output from the light source, outputs one beam of the branched light as pump light, and outputs another beam of the branched light as probe light, (3) a terahertz wave generation element which generates and outputs the terahertz wave by inputting the pump light output from the branch part, (4) a terahertz wave detection element which inputs the terahertz wave output from the terahertz wave generation element and passed through or reflected by a measurement object, inputs the probe light output from the branch part, and detects a correlation value between the terahertz wave and the probe light, (5) a delay providing medium which is disposed on an optical path of the terahertz wave from the terahertz wave generation element to the terahertz wave detection element, and is formed of a material of which a refractive index for the terahertz wave depends on the temperature, and provides a delay according to the temperature to the terahertz wave, (6) a temperature adjustment unit which adjusts the temperature of the delay providing medium, and (7) an analysis unit which obtains a temporal waveform of an electric field amplitude of the terahertz wave input to the terahertz wave detection element based on the correlation value detected by the terahertz wave detection element when the temperature adjustment unit has set the temperature of the delay providing medium to each value.

In the above apparatus, it is preferable that the delay providing medium input the terahertz wave from an input surface, allow the terahertz wave to be reflected and propagated internally, and then, output the terahertz wave from an output surface to the outside. Further, in the above apparatus, it is preferable that the delay providing medium have a reflection surface which changes the terahertz wave to parallel light or convergent light when the terahertz wave is reflected and propagated internally.

In the above apparatus, it is preferable that the delay providing medium be integrated with the terahertz wave generation element. Further, in the above apparatus, it is preferable that the delay providing medium be integrated with the terahertz wave detection element.

It is preferable that the terahertz wave temporal waveform acquisition apparatus further include a pulsed light guiding optical fiber for guiding the pulsed light from the light source to the branch part, a pump light guiding optical fiber for guiding the pump light from the branch part to the terahertz wave generation element, and a probe light guiding optical fiber for guiding the probe light from the branch part to the terahertz wave detection element.

It is preferable that the terahertz wave temporal waveform acquisition apparatus obtain an integrated value of the temporal waveforms by alternately performing acquisition of the temporal waveform of the electric field amplitude of the terahertz wave by changing the delay providing medium from a low temperature to a high temperature, and acquisition of the temporal waveform of the electric field amplitude of the terahertz wave by changing the delay providing medium from a high temperature to a low temperature. Alternatively, it is preferable that the terahertz wave temporal waveform acquisition apparatus obtain an integrated value of the temporal waveforms by alternately performing the acquisition of the temporal waveform of the electric field amplitude of the terahertz wave by increasing the temperature of the delay providing medium, and the acquisition of the temporal waveform of the electric field amplitude of the terahertz wave by decreasing the temperature of the delay providing medium.

It is preferable that the terahertz wave temporal waveform acquisition apparatus include a plurality of delay providing media as the delay providing medium, and obtain an integrated value of the temporal waveforms by arranging the plurality of delay providing media on the optical path of the terahertz wave from the terahertz wave generation element to the terahertz wave detection element one by one, and obtaining the temporal waveform of the electric field amplitude of the terahertz wave by setting the temperature of the arranged delay providing medium to each value.

The present invention can be used as a terahertz wave temporal waveform acquisition apparatus which can be easily downsized.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A terahertz wave temporal waveform acquisition apparatus comprising:
   a light source outputting pulsed light;
   a branch part branching the pulsed light output from the light source, outputting one beam of the branched light as pump light, and outputting another beam of the branched light as probe light;
   a terahertz wave generation element generating and outputting a terahertz wave by inputting the pump light output from the branch part;
   a terahertz wave detection element inputting the terahertz wave output from the terahertz wave generation element and passed through or reflected by a measurement object, inputting the probe light output from the branch part, and detecting a correlation value between the terahertz wave and the probe light;
   a delay providing medium disposed on an optical path of the terahertz wave from the terahertz wave generation element to the terahertz wave detection element, formed of a material of which a refractive index for the terahertz wave depends on the temperature, and configured to provide a delay according to the temperature to the terahertz wave;
   a temperature adjustment unit configured to adjust the temperature of the delay providing medium; and
   an analysis unit obtaining a temporal waveform of an electric field amplitude of the terahertz wave input to the terahertz wave detection element based on the correlation value detected by the terahertz wave detection element when the temperature of the delay providing medium is set to each value by the temperature adjustment unit.

2. The terahertz wave temporal waveform acquisition apparatus according to claim 1, wherein the delay providing medium inputs the terahertz wave from an input surface, allows the terahertz wave to be reflected and propagated internally, and then, outputs the terahertz wave from an output surface to the outside.

3. The terahertz wave temporal waveform acquisition apparatus according to claim 2, wherein the delay providing medium has a reflection surface which changes the terahertz wave to parallel light or convergent light when the terahertz wave is reflected and propagated internally.

4. The terahertz wave temporal waveform acquisition apparatus according to claim 1, wherein the delay providing medium is integrated with the terahertz wave generation element.

5. The terahertz wave temporal waveform acquisition apparatus according to claim 1, wherein the delay providing medium is integrated with the terahertz wave detection element.

6. The terahertz wave temporal waveform acquisition apparatus according to claim 1, further comprising:
   a pulsed light guiding optical fiber guiding the pulsed light from the light source to the branch part;
   a pump light guiding optical fiber guiding the pump light from the branch part to the terahertz wave generation element; and
   a probe light guiding optical fiber guiding the probe light from the branch part to the terahertz wave detection element.

7. The terahertz wave temporal waveform acquisition apparatus according to claim 1, wherein
   an integrated value of the temporal waveforms is obtained by alternately performing acquisition of the temporal waveform of the electric field amplitude of the terahertz wave by changing the delay providing medium from a low temperature to a high temperature, and acquisition of the temporal waveform of the electric field amplitude of the terahertz wave by changing the delay providing medium from a high temperature to a low temperature.

8. The terahertz wave temporal waveform acquisition apparatus according to claim 1, comprising a plurality of delay providing media as the delay providing medium, wherein
   an integrated value of the temporal waveforms is obtained by arranging the plurality of delay providing media on the optical path of the terahertz wave from the terahertz wave generation element to the terahertz wave detection element one by one, and obtaining the temporal waveform of the electric field amplitude of the terahertz wave by setting the temperature of the arranged delay providing medium to each value.

\* \* \* \* \*